(12) United States Patent
Chase et al.

(10) Patent No.: US 6,710,877 B2
(45) Date of Patent: Mar. 23, 2004

(54) APPARATUS AND METHODS FOR DETERMINING BIOMOLECULAR INTERACTIONS

(75) Inventors: Christopher J. Chase, Apalachin, NY (US); Peter J. Kalal, Corning, NY (US); Mark A. Quesada, Horseheads, NY (US); Youchun Shi, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 21 days.

(21) Appl. No.: 09/911,119

(22) Filed: Jul. 23, 2001

(65) Prior Publication Data

US 2003/0016360 A1 Jan. 23, 2003

(51) Int. Cl.[7] ................................................ G01N 21/00
(52) U.S. Cl. ........................ 356/432; 356/336; 356/445
(58) Field of Search ................................ 356/432, 335, 356/336; 256/445

(56) References Cited

U.S. PATENT DOCUMENTS

| | | | | |
|---|---|---|---|---|
| 4,815,843 A | | 3/1989 | Tiefenthaler et al. | 356/128 |
| 5,007,737 A | * | 4/1991 | Hirleman, Jr. | 356/336 |
| 5,071,248 A | | 12/1991 | Tiefenthaler et al. | 356/128 |
| 5,118,608 A | * | 6/1992 | Layton et al. | 435/7.1 |
| 5,479,260 A | | 12/1995 | Fattinger | 356/361 |
| 5,528,045 A | * | 6/1996 | Hoffman et al. | 250/458.1 |
| 5,671,303 A | * | 9/1997 | Shieh et al. | 385/12 |
| 5,738,825 A | | 4/1998 | Rudigier et al. | 422/82.11 |
| 5,776,674 A | * | 7/1998 | Ulmer | 435/6 |
| 5,812,272 A | * | 9/1998 | King et al. | 356/445 |
| 5,949,532 A | * | 9/1999 | Schrof et al. | 356/73 |
| 6,025,202 A | * | 2/2000 | Natan | 436/104 |
| 6,110,749 A | * | 8/2000 | Obremski et al. | 436/527 |
| 6,151,123 A | * | 11/2000 | Nielsen | 356/445 |
| 6,416,959 B1 | * | 7/2002 | Giuliano | 356/326 |
| 6,458,547 B1 | * | 10/2002 | Bryan et al. | 356/215 |
| 6,462,809 B1 | * | 10/2002 | Ryan et al. | 356/128 |

* cited by examiner

Primary Examiner—Diane I. Lee
Assistant Examiner—Ahshik Kim
(74) Attorney, Agent, or Firm—Scott S. Servilla; Vincent T. Kung

(57) ABSTRACT

Methods, apparatus and substrates for the detection of reactions between biomolecules or cells and a second compound are disclosed. The invention detects interactions between ligands and receptors by utilizing detecting the diffusion of a species proximate a sensing area. Absorbance detection and diffraction sensors are utilized to monitor the rate of diffusion from the sensing area.

34 Claims, 13 Drawing Sheets

APPARATUS AND METHODS FOR DETERMINING BIOMOLECULAR INTERACTIONS

FIELD OF THE INVENTION

This invention relates to sensing of diffusion of biomolecules. More particularly, the present invention relates to substrates, apparatus and methods for monitoring and detecting interactions between a ligand and a receptor.

BACKGROUND OF THE INVENTION

The drug discovery process is a highly risky venture. The Pharmaceutical Research and Manufacturers of America estimate the average time to bring a drug to market is approximately 12 to 15 years at an average cost of approximately 500 million dollars. Among US pharmaceutical companies, more than 100 new therapeutic treatments have been added to the available medicines in the last two years. Among the many sequence of events applied in the pharmaceutical industry to realize commercially successful products, high-throughput screening (HTS) is believed to be an essential cornerstone of an effective drug discovery strategy. The HTS market in 1998 was estimated at 1.6 billion dollars.

High-throughput screening (HTS) refers to the initial activity in the pharmaceutical development process that systematically compares the binding of a target molecule or compound with each compound archived in a pharmacophore compound library. These libraries may contain millions of potential drugs acquired from a variety of sources, natural or otherwise, that are systematically screened for bioactivity against target molecules or compounds. The remarkable biological and biochemical advances of the last decade at the cellular and molecular levels have created numerous opportunities for discovery by uncovering an abundance of new receptors and enzymes that are mechanistically associated with disease pathologies. As these new targets emerge, a demand on analytic capacity to screen the targets against the large compound libraries for "hits" becomes a tremendous logistical effort.

The development of a technology applying direct binding assays (DBA) to high-throughput screening (HTS) could capture a significant share of the market for HTS. Surface-plasmon resonance (SPR) is a popular DBA technique in the pharmaceutical industry. SPR is but one of a large class of optical biosensors collectively referred to as evanescent wave detectors. This class includes film waveguide grating couplers, film prism waveguide couplers and long-period fiber waveguide couplers. The essential feature of all these techniques is that a standing "evanescent" wave is generated above the sensing surface by a wavelength's distance from the surface (approximately 100–200 nm) that is sensitive to the local dielectric environment. By changing the local refractive index, the standing wave is altered, requiring either a new angle of incident light to set up the "resonance condition" or inducing a phase shift of the reflected light. Since all proteins, independent of sequence, contribute the same refractive index per unit mass, this technique can serve as a mass detector. A linear correlation between resonance angle shift and surface protein concentration has been demonstrated, allowing real time detection of mass change without the need for labeling. All evanescent wave techniques are variations on this essential theme.

To distinguish between molecules floating in the bulk solution from those molecules attached to surface-bound target molecules, evanescent-based biosensors require that one flows buffer solution over the sensing surface after having flowed the buffer/analyte solution to infer the presence of surface bound analyte. Measurement of the adsorption in real time requires complex fluidic control of different flow conditions and solutions to infer the association rate constants from the observed binding rates. This is because evanescent-based methods do not distinguish between molecules floating in the evanescent standing wave and molecules anchored to the substrate also present in the evanescent field.

Another limitation of evanescent wave methods is that they do not readily lend themselves to miniaturization. In addition, light is invariably coupled into substrates with non-zero angles-of-incidence, often requiring complex schemes to measure extremely small shifts in reflected light or inducing small angular shifts in the incident light. Such limitations make massive deployment of similar sensing elements on small chips extremely problematic.

It would be desirable to provide substrates, apparatus and methods that do not encounter the drawbacks of evanescent-wave based methods. Many drugs are small molecules in the range between 200–1000 Dalton with binding affinities in the range between $10^{-6}$ and $10^{-12}$ M. Therefore, it would be advantageous to provide methods and apparatus capable of characterizing small-drug and target-protein binding interactions. It would also be advantageous to provide HTS methods and apparatus that are capable of being "homogeneous and label-free" and provide the same information content as the more labor-intensive methods discussed above.

SUMMARY OF INVENTION

The invention relates to assay methods and apparatus for monitoring biological or chemical interactions by providing means to monitor and/or detect diffusion proximate a sensing area. According to the present invention, the interactions between and among chemicals, cells and biomolecules can be detected by monitoring the diffusion of a molecule or chemical proximate a sensing area. Such diffusion monitoring provides the ability to detect and measure interactions between ligands and receptors, such as a protein molecule or a cell.

According to one aspect of the invention, an apparatus is provided that measures rate of diffusion proximate a sensing area. According to another aspect of the invention, the rate of diffusion may be measured by several means. For example, the rate of diffusion proximate the sensing area may be measured by monitoring the concentration of a molecule proximate the sensing area. One example of such an apparatus may include a first area that may optionally contain a matrix material and receptor molecule or cell contained in the first area. The matrix material can be any suitable matrix for the receptor, such as a polymeric matrix material. According to this aspect of the invention, the apparatus preferably includes a second area adjacent the first area and a boundary area is disposed between the first and second areas. According to this aspect of the invention, preferably a ligand molecule is contained in the first area with the receptor and the matrix material. The second area preferably contains a solution such as a buffer solution.

According to another aspect of the invention, the ligand is smaller than the receptor. For example, the ligand molecule may be a drug molecule having a molecular weight less than 1000 Daltons, and the receptor has a molecular weight greater than 5 kiloDaltons. According to another aspect, the boundary area includes a membrane operative to allow ligand molecules to pass therethrough and to prevent passage of receptor molecules In another aspect of the invention, the receptor includes a protein molecule. It is understood that the invention is not limited to any particular ligands and receptors. As such, the receptors could include a wide variety of biomolecules including, but not limited to proteins, nucleic acids, and cells.

According to still another aspect of the invention, the means for detecting the diffusion of the molecules or cells includes an optical detector. A wide variety of suitable optical detection systems can be used in accordance with the present invention. For example, a light source and a light detector can be used. The light source may be, for example, an ultraviolet (UV) light source, and the light detector can be a charge-coupled light detector. According to this aspect, the light may be directed towards the second area, and the optical detector is positioned and operative to measure the change in light absorbed by the second area.

According to another embodiment of the invention, the means for detecting the rate of diffusion of the molecules or cells includes a diffraction device that includes three laterally-spaced openings, slits or slots. The laterally-spaced openings or slots may be provided on a suitable substrate. According to this aspect of the invention, the means for detecting the rate of diffusion of the molecules or cells involves monitoring the change in the far-field diffraction pattern generated by the diffraction device. According to a preferred aspect of the invention, the three laterally spaced openings includes a central opening containing a ligand and receptor in solution. According to this aspect, means are provided for detecting the change in the concentration of the ligand and the receptor contained in the central opening. The means for detecting the change in concentration may include a charge-coupled device (CCD) camera or other suitable device for monitoring the change in the diffraction pattern generated by the three laterally spaced openings as the ligand diffuses from the central opening.

According to another aspect of the invention, a method of analyzing biomolecular binding is provided, which involves detecting the diffusion of biomolecules proximate a slotted diffraction surface. The slotted diffraction surface may include three laterally spaced slots or openings, or any other arrangement capable of producing a far field diffraction pattern. According to one aspect of the invention, a central slot is provided and a ligand and receptor in solution are positioned proximate the central slot.

Another aspect of the invention involves monitoring the rate of diffusion of ligands from an upstream area towards a downstream area. Preferably, the upstream area includes an upstream compartment containing a mixture of a ligand and a receptor. The ligand and receptor are preferably contained in a matrix material, for example, a polymeric matrix. Diffusion of the ligand and receptor towards the downstream area can be measured by measuring the change in absorbance of light in the downstream compartment. As a greater amount of ligand and receptor diffuse towards the downstream area, the absorbance of light in the downstream area will increase. The absorbance characteristics can be utilized to detect & quantify the binding between a ligand and a receptor.

The invention provides a relatively simple and flexible method to detect chemical reactions, biomolecular reactions, particularly interactions between ligands and receptors, thus facilitating high throughput screening of biomolecules and drug candidates. Direct sensing of ligand-receptor binding can be measured without the need for introducing fluidics. In contrast, evanescent wave detectors typically require flow of buffer solution over the sensing element after having flowed the buffer/analyte solution to infer the presence of surface bound analyte. It is envisioned that the present invention can be combined with fluidics techniques. It will be understood, however, that analysis of binding between a wide variety of ligands and receptors can be accomplished without resort to fluidics techniques.

The embodiment of the invention involving monitoring the diffraction pattern also has the advantage that many 3-slit sensing elements on small substrates are possible because of the small lateral dimensions attainable by the zero angle-of-incident design. In addition, it is possible to obtain high-sensitivity (in the range of two orders of magnitude) by introducing a quarter wave trough or raised-surface on the central slit of the tri-slit device. Furthermore, sensitivity is not compromised by thermal expansion of materials used to construct the device under room temperature operational conditions.

Additional advantages of the invention will be set forth in the following detailed description. It is to be understood that both the foregoing general description and the following detailed description are exemplary and are intended to provide further explanation of the invention as claimed.

DETAILED DESCRIPTION

Figure 1:
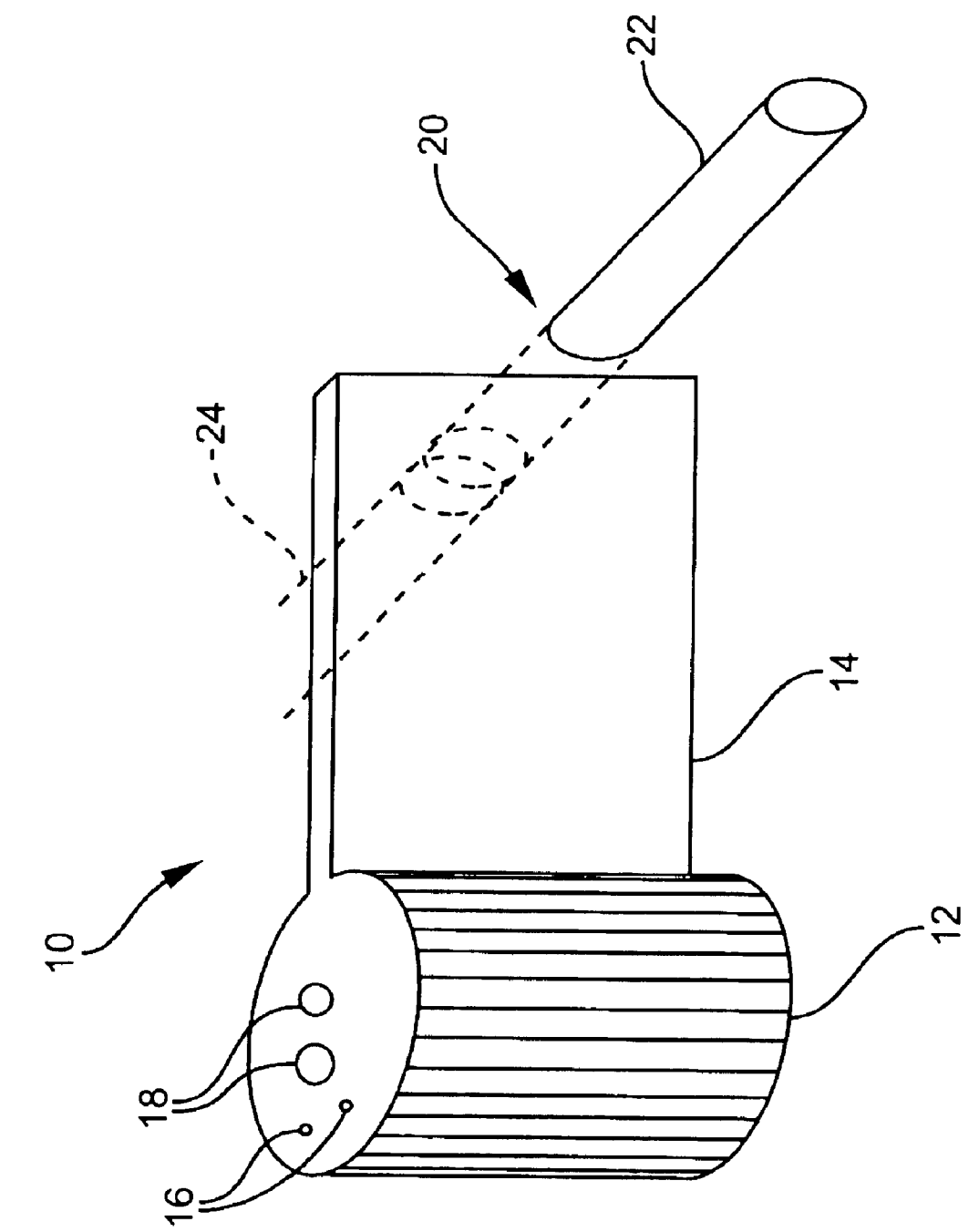
FIG. 1 shows a schematic representation of an apparatus for monitoring the diffusion of species from an upstream area towards a downstream area.

The present invention relates to apparatus, substrates and methods for analyzing interactions between ligands and receptors. As used herein, ligand refers to an ion or molecule that binds to another chemical or biological entity to form a larger complex. As used herein, the term receptor means an entity that binds to a ligand, which can include a wide variety of biomolecules and cells. As used herein, the term "substrate" refers to a sample holder or container suitable for use in the measurement of interaction between chemical or biomolecules in an array of locations. Such a substrate, can include, for example, a glass or plastic slide, a microfluidics chip, a microplate or a microarray chip suitable for use in high throughput screening of biomolecular interactions.

According to the present invention, diffusion of species towards the sensing area of a concentration detector may be used for assessing ligand-receptor binding. A mixture of suitable matrix material, for example, a low-melt agarose gel, a ligand, such as a drug molecule, and a receptor, such as a protein molecule, are placed in the sensing area of the device and the ligand, the receptor and/or their conjugate diffusion or leaching is monitored over time. The time required to cease reach steady-state or leaching over sensing area, in the presence of receptor, is found to be characteristic of the receptor-binding affinity. An advantage of the invention is that no labeling chemistry is required for the ligand, receptor or any of the constituents to carry out a binding analysis.

According to the present invention, the concentration may be monitored using a variety of methods and apparatus. In one example, the build up of drug in a sensing area, for example, a compartment, downstream of the gel-interface using a light source, such as, for example, ultra-violet light source. In another example, the diffusion of a ligand from a sensing area of a diffraction device containing three optical holes is monitored. In this latter case, the far-field diffraction pattern has a characteristic shape that is sensitive to changes of the refractive index in the central sensing area. While the invention should not be limited by a particular theory of operation, it is believed that use of a sufficiently dense matrix, such as agarose gel, immobilizes a receptor such as a protein while a ligand, for example a drug molecule, traverses the polymer network by random-walk, Brownian motion. The invention enables the manufacture of relatively simple sensors that can be miniaturized to very small dimensions (as low as 500 microns and smaller). The invention does not require sophisticated microfluidics, thus facilitating the prospect of producing high-density, high-throughput devices for drug-screening.

The present invention provides a biological and chemical sensor capable of performing high throughput screening and characterizing small-drug and target-protein binding interactions. Many drugs are small molecules in the range between 200 and 1000 Dalton with binding affinities in the range between $10^{-6}$ M to $10^{-12}$ M. The present invention provide a homogeneous and label-free assay that provides the same information content as more labor-intensive methods.

A distance a species (for example, a molecule, an ion or a cell) travels due to diffusion is a function of time and its diffusion coefficient. Large differences in size between a ligand, such as a drug molecule, for example, having a molecular weight less than 1000 Dalton and a receptor, such as a protein, having a relatively large molecular weight, for example, greater than 5 kiloDaltons, can be used to determine ligand-receptor binding based on the rate of diffusion.

A variety of detection methods and apparatus can be used to determine the rate of diffusion of ligands, receptors, and their conjugates. Electrical and optical methods, or combinations of these methods are known in the art and can be utilized to measure the rate of diffusion. As one example, the change in absorbance of a sensing area can be measured to determine whether ligand, receptor, or their conjugates have diffused to or from a reaction area.

There are a wide variety of arrangements that can be utilized according to the present invention. An example of such an arrangement of a sensing apparatus 10 is shown in FIG. 1. The apparatus 10 includes a first region 12 and a second region 14. The first region 12 could include a compartment or other suitable area for containing a ligand 16 and a receptor 18 in an appropriate solution. The solution could be a buffer solution or a polymeric matrix. The ligand 16 and the receptor 18 can be a wide variety of species. The ligand 16 and receptor 18 could be complementary binding pairs of biomolecules. For example, the ligand 16 could be a drug molecule and the receptor 18 could be a protein molecule. It will be understood that the invention is not limited to any particular ligand and receptor species. For example, it is contemplated that the present invention could be utilized to analyze and detect binding between antibodies and antigens, the formation of nucleic acid complexes, as well as the binding of other species.

Still referring to FIG. 1, a suitable detector 20 can be employed to monitor the diffusion of the ligand 16 and the receptor 18 in the second region 14. As noted above, if the size of the ligand 16 and the receptor 18 are known, their diffusion coefficients will be known or can be determined experimentally. If the ligand 16 is a small drug molecule, it will have a high rate of diffusion through the solution or the matrix material. If the receptor is a larger molecule, it will have a slower rate of diffusion. According to one embodiment of the invention, the detector 20 may include a light source 22, such as a UV light source, positioned on one side of the second region 14 of the apparatus 10. A camera or monitor 24 positioned on the opposite side of the second region measures the absorbance of the light in the second region 14 of the apparatus. By monitoring the change in the absorbance of light in the second region 14, the rate of diffusion of the ligand 16 and the receptor 18 can be determined. The second region 14 thus becomes a sensing area for determining the rate of diffusion of the ligand 16 and the receptor 18 and/or their conjugate.

If a mixture of the ligand 16 and the receptor 18 at a selected specific concentration ratio are placed proximate a sensing area, the diffusion pattern from or towards the sensing area will be influenced by whether the ligand 16 and the receptor 18 bind. The concentration of the ligand 16, the receptor 18 and their conjugate will be measured proximate the sensing area. In the case of non-binding species, movement of the smaller molecule having a much higher mobility will be detected first, and movement of the larger molecule species will be detected later because of its lower mobility. Thus, two widely spaced signals will be detected when the ligand and the receptor do not interact or bind. When the ligand and receptor bind, however, the smaller molecule ligand will not be detected as a singly diffusing species, but as a signal at a much later point in time compared with an unbound ligand signal.

As an example, drug leaching or diffusion from a solution or matrix material such as an agarose gel into an adjacent area containing a fluid can be modeled. The matrix material containing both a drug and a dispersed drug-binding protein leaches the low-molecular weight drug from the matrix/fluid interface into a "well-stirred" fluid of limited volume $V_{soln}$. "Well-stirred" implies that the drug concentration in the fluid is uniform and equal to that at the interface. It is also assumed that the fundamental drug transport mechanism is Brownian motion in the midst of an effective matrix containing protein molecules. The matrix serves simply to lock the larger proteins in place while the polymeric-sugar character of agarose matrix minimizes adhesion of drugs. The drugs themselves are typically very mobile since they typically range from 200 to 1000 Dalton in contrast to average target proteins that span the range from 10,000 to 100,000 Dalton.

Brownian motion in the absence of any binding events may be simply described by the continuity expression $\partial c/\partial t = D \cdot \nabla c$, wherein $\partial c/\partial t$ is the change in concentration over time, D is the diffusion coefficient and $\nabla c$ is the change in concentration divergence. To account for binding and non-specific binding events during Brownian transport, additional considerations must be taken into account.

A general solution to the diffusion of molecules undergoing a reversible reaction was derived in Crank, J., *Mathematics of Diffusion*. 1956, Oxford: Clarendon Press. 347, using Laplace transform methods. The solution contains a series expansion of trigonometric and exponential terms having temporal, spatial, reactive and diffusional parameters as arguments. The individual influence of these parameters is not clear with such an expression. Instead, making the assumption that there is an "effective rate" constant describing the apparent loss of molecules, as if they all truly underwent a first order rate loss (e.g., -kc). Strong binding affinities would still be reflected in relatively large "effective rate" constants and low binding affinities would have relatively small "effective rate" constants. Adopting this perspective, then the time rate of change in the continuity equation must reflect the fact that, at any given location, there is a probability that the drug molecule randomly walking through a matrix or "minefield" of binding sites will be in a bound, or immobile, state. This assumption is expressed by adding a first-order reactive contribution to the continuity equation: $dc/dt = -k_{eff} \cdot c \cdot P$. P is the protein concentration. This rate constant may contain a binding component, $k_b$, and a non-specific binding component, $k_{nsb}$, such that $k_{eff} = k_b + k_{nsb}$. This suggests that two experiments should be run: One that measures the non-specific binding using a known non-binding ligand, and another that measures more of the binding if the drug has a binding affinity greater than non-specific binding. The difference observed from both experiments should be linearly related to the binding affinity. In other words, the difference measurement should reflect the degree to which the putative drug binds with an affinity greater than simple non-specific binding.

Combining the above considerations into the following governing equation:

$$\partial c/\partial t = D \cdot \partial^2 c/\partial x^2 - k \cdot c \qquad (1)$$

subject to the following boundary conditions: At t=0, the initial drug concentration, $c_0$, is constant everywhere in the matrix and zero otherwise; the "well-stirred" boundary condition at x=a and t>0 implies that all drugs, c, that make it to the matrix/fluid interface are instantly mixed into the volume $V_{soln}$. (i.e., the molecular flux at x=a is: $D \cdot A(dc/dx) = V_{soln}(dc/dt)$). The terms D and k in equation (1) and the boundary conditions refer to the effective drug diffusion constant in the matrix and the "effective microscopic association rate constant" (described above) respectively. The effective diffusion constant reflects drug diffusion through the matrix in the absence of binding protein and the "effective microscopic association constant" accounts for all rate processes that make the diffusing ligand immobile. The term A in boundary condition refers to the lateral area of the matrix interface in contact with the liquid volume towards which the species is diffusing. Equation 1 also assumes the matrix lateral dimensions (x and y, which are perpendicular to the direction of diffusion) are sufficiently small compared to the longitudinal dimension (z, which is parallel with the direction of diffusion) to safely approximate the diffusional dynamics with the x dimension alone while still retaining the fundamental physical behavior.

By solving this equation with the boundary conditions described above, the following analytic expression for the drug concentration at any x-position in the matrix material for t>0 is obtained:

$$C(x,t) = e^{-kt} \cdot c_0/2 \, Erfc((x-a)/\sqrt{4Dt})) \qquad (2)$$

where Erfc refers to the complementary error function described in Basmadjian, D., *The Art of Modeling in Science and Engineering*. 1999, Boca Raton: Chapman & Hall/CRC. 654.

The experimental observations made according to equation (2), require monitoring the unsteady concentration profiles in the matrix material. Instead, the more tenable experiment would merely require that we monitor the fractional release, $M_t/M_\infty$, of drug into the second area. Here, $M_t$ denotes the total amount of drug released up to time t, $M_\infty$ the same quantity at infinite time. $M_t$ is obtained from the concentration profiles, c(x,t), as follows:

$$M_t = -D \cdot \int_0^t (\partial c/\partial x)_{|x|=a} \partial t = \sqrt{(D/4K)} \cdot A \cdot (c_0/2) \cdot Erf[\sqrt{(k \cdot t)}] \qquad (3)$$

To better visualize operation of the present invention, an example of binding between a large receptor such as a protein, myosin, and a small molecule, such as glycine, is provided. Myosin has a molecular weight of 493,000 Dalton and a diffusion coefficient of $0.116 \times 10^{-10}$ m$^2$/s, and glycine has a molecular weight of 75 Dalton and a diffusion coefficient of $10 \times 10^{-10}$ m$^2$/s. If myosin and glycine are mixed together in a suitable biochemical buffer, myosin would need 430 seconds to travel 100 microns, while the glycine could travel the same distance in approximately 5 seconds. If glycine binds to the larger molecule myosin in solution, the resulting complex will diffuse through the solution at a rate comparable to the myosin.

An alternative to the detection scheme shown in FIG. 1 may involve moving the light source 22 and the camera or monitor 24 to measure the rate of diffusion from the first region 12. In this situation, the camera or monitor 24 could be set up to measure the decrease in absorbance in the first region 12. In another detection scheme, instead of providing a mixture of ligand and receptor in free solution in the first sensing area, either the ligand or the receptor could be immobilized in the first region, and a potential binding partner could be placed in the first region. In this situation, binding would be indicated by the absence of the binding species in the second region, and the failure of the species to bind would be indicated by detection of the binding species in the second region.

Figure 2:
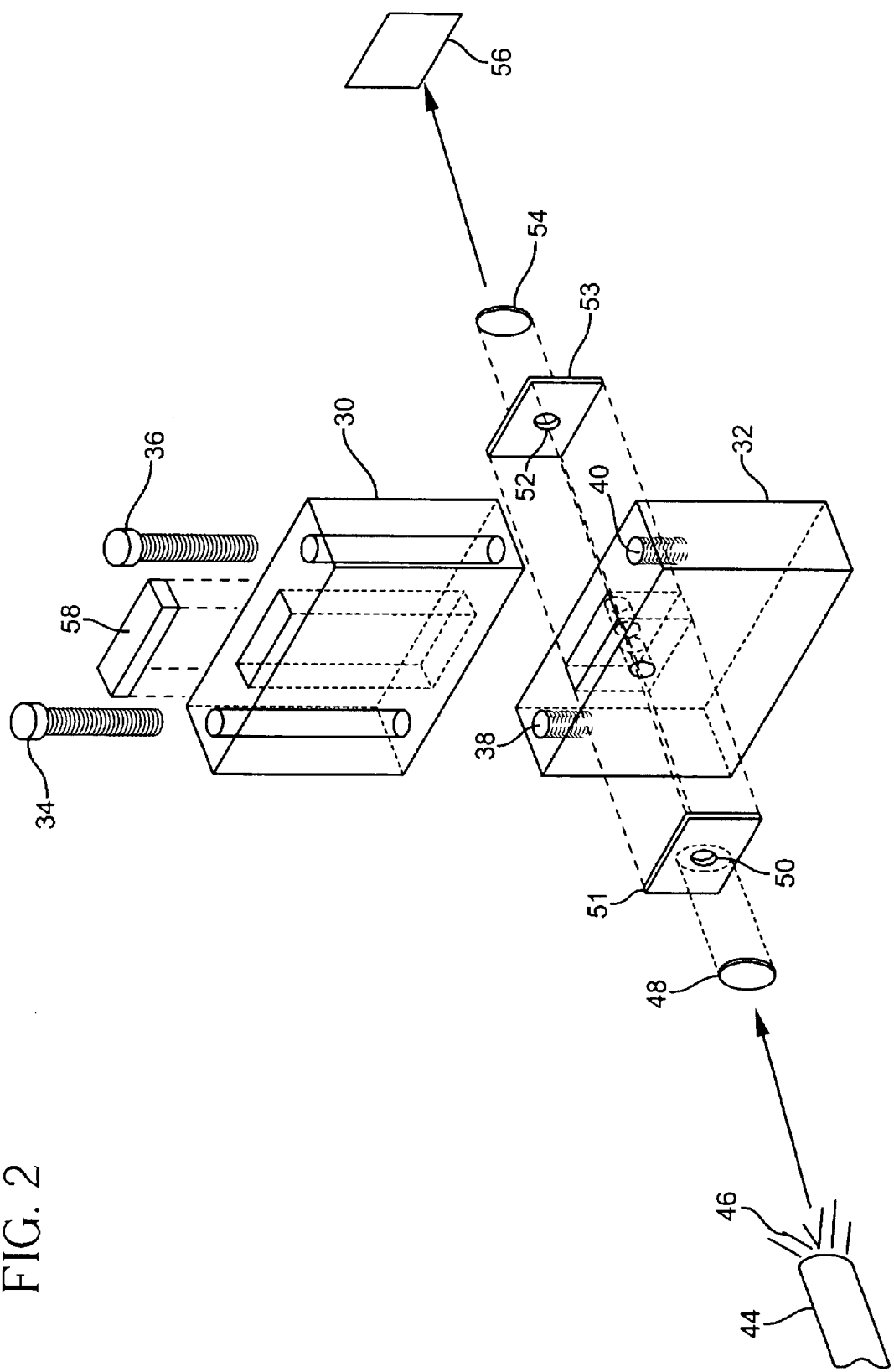
FIG. 2 shows schematic representations of an apparatus for monitoring diffusion from an upstream compartment towards a downstream compartment.

Referring now to FIG. 2, an alternative arrangement for detecting binding between a ligand and receptor is shown. A first, "upstream" compartment 30 and a second, "downstream" compartment 32 are provided. The first and second compartments can be manufactured from any suitable materials such as glass, metal, ceramic, polymeric materials, or combinations thereof. Assembly of the first compartment 30 and the second compartment 32 may be facilitated by an appropriate attachment mechanism such as screws 34 and 36, which respectively engage threaded openings 38 and 40 contained in the second compartment 32. It will be understood that other appropriate mechanisms can be used to attach the first compartment 30 and the second compartment 32, such as clips, adhesive, etc.

Light source 44, for example, a 220 nm xenon lamp, directs light 46 through a first lens 48, which may be made from silica or another suitable material, attached over a first opening 50 in a gasket 51 attached to the second compartment 32. On the side of the second compartment 32 opposite the first gasket 51, a second hole 52 in a second gasket 53 and a second silica lens 54 direct light towards a detector 56. The detector can be any appropriate detector, for example a CCD detector. The first compartment may be sealed with an appropriate seal 58 such as a gasket.

It will be understood that a wide variety of arrangements could be utilized to implement the invention in addition to the arrangements described immediately above. For example, two adjacent microplate wells connected by conduit could be utilized to implement the present invention. A first well containing ligand and receptor in an appropriate matrix material could be connected to an adjacent well containing a buffer solution. If the two wells were connected, the rate of diffusion from the first well through the conduit and into an adjacent well could be measured.

Figure 3:
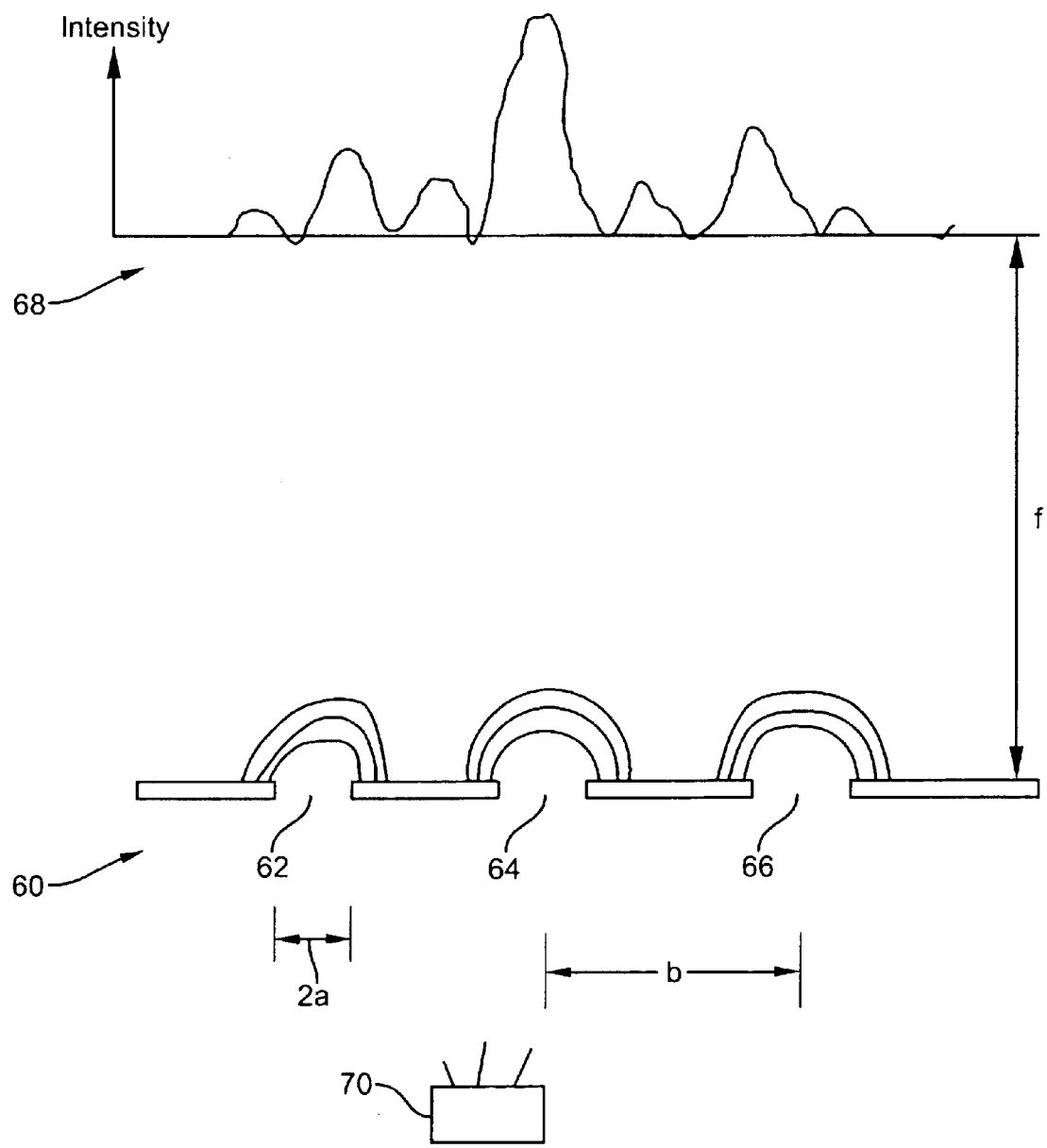
FIG. 3 schematic view of diffraction sensor according to one embodiment of the invention.

Another embodiment of the invention relates to the diffusion of ligand from a diffraction device. Referring now to FIG. 3, one example for implementing this embodiment may include a three-slit diffractor 60. Three slits 62, 64, and 66 may be microfabricated on a translucent substrate having a separation distance, b, a slit width $2a$, and separated from an observation plane 68 distance f away from the three slits. The observation plane is a sufficient distance away such that the Fraunhofer diffraction condition applies and we may safely describe the diffraction in the far-field using Fourier optics.

If we simultaneously illuminate the three slits with a single light source 70, the intensity pattern in the plane of observation may be described as $4a$ sinc(kaxlf)[1+4 cos (kbxlf)+4 cos(kbx/f)], where $k=2\pi r/\Lambda$ with $\Lambda$ corresponding to the wavelength of the incident light. The interference pattern is similar, though different, to the intensity distribution illustrated above. In the absence of the sinc function envelope, this is simply $$Int \approx 1+4 \cos^2(kbxlf)+4 \cos(kbx/f) \qquad (5)$$

If a divot is made on the central slit deep enough to confer a phase shift of $-\pi/2$, a new intensity pattern is provided that is due to solely to molecules attaching to the central slit and conferring a phase shift $\epsilon$ as $$Int \approx 1+4 \cos^2(kbx/f)+4 \cos(kbx/f)\sin(\epsilon) \qquad (6)$$

When the difference in intensity of two consecutive peaks is measured, the difference $\Delta Int$ may be expressed as $$\Delta Int = 8 \sin(\epsilon) \text{ or } \Delta Int/\Delta Int_{max} = \sin(\epsilon) \approx \epsilon \text{ for small } \epsilon \qquad (7).$$

When measuring peak intensity of the slits when the central slit contains a solution containing molecules, this clearly indicates that the measurement of the consecutive peak intensity difference is directly related to the phase shift associated with molecules adhering to the central slit and not the refractive index of the bulk solution containing the molecules. This is to be contrasted with evanescent wave techniques which measure everything in the 200 to 300 nm area above the sensing surface and require additional measures to separate the true adsorption measurement from the "bulk effect". This 3-slot method minimizes or eliminates bulk effects as long as the optical path from each slit is identical except for the small phase shift $\epsilon$ associated with molecules attaching to the central slit.

An immediate implication of equation 7 is that no additional reference measurement needs to be built to account for temporal intensity fluctuations. This is because $\Delta Int$ is related to the difference between intensities of different parts of the same pattern and not a solitary intensity measurement. Consequently, regardless of intensity fluctuations, $\Delta Int$ can always be measured.

The fundamental limitation to measuring $\Delta Int$ in equation 7 is the inherent noise of measuring a diffracted laser beam or other similar light source. Technology available today makes this type of measurement possible with close to shot-noise limited performance. A sensitive imaging detector, such as a scientific-grade CCD detector, should be able to provide intensity measurements approaching $\Delta Int/\Delta Int_{max}=100/65000$ (e.g., Andor-Technology CCD detectors). This level of performance of the imaging-detector dictates the fundamental limit of the method which is $$\epsilon = \pi/2042 \qquad (8).$$

If a helium-neon laser ($\Lambda=632$ nm) were used, equation 8 indicates that the minimum, experimentally realizable phase shift detected would correspond to a change of thickness equal to 1.5 angstroms.

The intensity difference between adjacent peaks in the diffraction pattern changes in accord with refractive index changes occurring in the central slot. Unlike Young slit diffraction patterns, the three-slot diffraction pattern does not spatially shift in the far-field but remains stationary. The degree to which the intensity difference changes between adjacent peaks due to refractive index changes in the central sensing volume may be expressed with the following relationship:

$$\Delta Int(\text{adjacent peaks}) \approx 8 \cdot \sin((2\pi/\lambda) \cdot L \cdot (\partial n/\partial c) \cdot \Delta c) \qquad (9),$$

where "$\Delta$ Int. adjacent Peaks" refers to the intensity difference between adjacent peaks, $\lambda$ corresponds to the wavelength of the incident light, L refers to the path length traversed by the incident light, $\partial n/\partial c$ refers to the change of refractive index as a function of changing concentration, and $\Delta c$ refers to the change of concentration. It should be noted that virtually all proteins have $\partial n/\partial c \sim 0.18 \pm 0.02$ mL/g and reflects the linear relationship between refractive index and mass. This relationship is traditionally exploited for analytical purposes to monitor mass changes for a specific sensing application (e.g., surface plasmon reflectance analysis, reflectance interferometric spectroscopy, etc.) other than protein sensing.

Figure 4B:
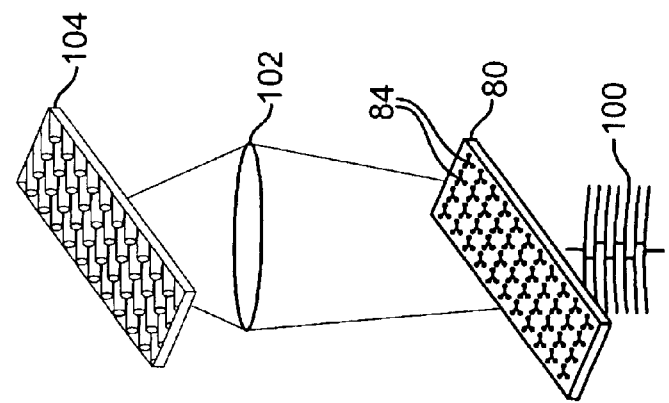
FIGS. 4A–4B are schematic views of another embodiment of a diffraction sensor.
Figure 4A:
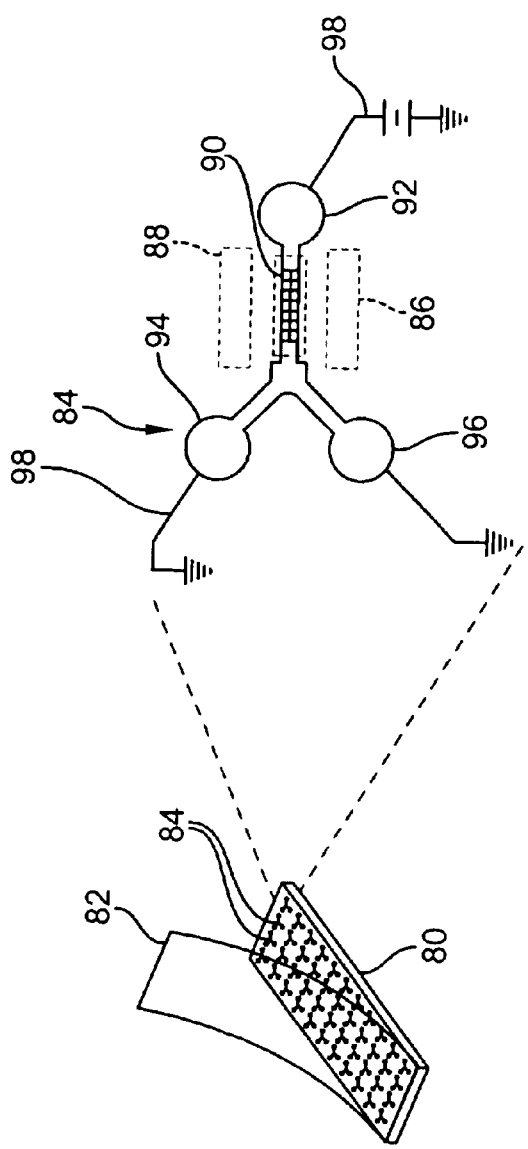

An example of an apparatus that could be used for mass analysis of binding of ligands and receptors is shown in FIGS. 4A and 4B. A slide 80 including a retractable transparent sheet 82 is provided. Multiple embossed Y-shaped elements 84 are provided on one side of the substrate. The other side of the substrate is opaque except for a 3-slit diffraction structure that is provide under or optically aligned with each of the sensing areas for each element 84. The three slits include two side slits 86 and 88 and a central slit 90 positioned under a sensing area 92 of the Y-shaped structure. The entire Y-shaped elements could be filled with buffer solution, and a first branch 94 could be filled with ligand molecules and a second branch 96 could be filled with receptor molecules. An electrokinetic pump 98 could be utilized to move solutions through the sensing area 92.

This structure, having multiple Y-shaped elements 84, could be illuminated by a light source 100, and a CCD camera 102 could detect a far-field diffraction pattern 104. The binding or non-binding of ligands and receptors could be monitored as they traverse the sensing area 92.

All three of the leads of the electrokinetic pump 98 could connected to each Y-shaped element 84 to enable parallel operation of all of the Y-shaped elements 84. In use, a target protein/gel mixture in the sensing area 92 of the Y-shaped elements 84, and then closing the retractable sheet 82 to inhibit evaporation. Thereafter, the retractable sheet 82 could be lifted, different drug molecules could be printed or otherwise deposited in designated compartments, and the retractable sheet could be closed. Parallel operation would occur by first flowing drug over the sensing area 92, followed by flow of buffer to wash any drug that does not bind to the target protein. Simultaneous monitoring of all of the Y-shaped elements 84 would proceed during regular intervals throughout the flowing operations to determine the occurrence or non-occurrence of ligand-receptor binding.

Without intending to limit the invention in any manner, the present invention will be more fully described by the following examples.

EXAMPLES

Example 1

Preparation of Gel Mixtures

Gel mixtures used in the following examples were prepared as follows. Metaphor™ agarose (Metaphor™; FM Laboratories, NH) was used exclusively for experiments requiring agarose. Glutamine and biotin were purchased from Sigma (G9003, B4501; Sigma Corp., St. Louis, Mo.) and used directly without further purification. Streptavidin was also obtained from Sigma corporation (B3763; Sigma Corp., St. Louis, Mo.) but dialyzed for two days against a 1×TBE buffer (BP1333-1; Fisher Corp., Chicago, Ill.) for the experiments conducted with diffraction measurements. Streptavidin was left undialyzed with the absorbance experiments. The sodium citrate buffer, 0.1×SSC (1-666-61; Roche Diagnostic Corp, Indianapolis, Ind.) was analytical grade and no further purification was performed. Anti-biotin (B3640; St. Louis, Mo.) was also used directly without dialysis.

Two general types of gel mixtures were used: agarose-gel systems containing streptavidin or agarose-gel systems containing anti-biotin. The concentration of streptavidin or anti-biotin was the same in either case, $8.2 \times 10^{-4}$ M. Streptavidin or anti-biotin were used to simulate target proteins commonly used in drug-screening efforts, typically in the range between 10,000 to 100,000 Dalton. The 2.5% agarose gels containing anti-biotin, and either biotin or glutamine in a 0.1×SSC buffer was used exclusively with the absorbance experiments. The 2.5% gels containing streptavidin, and either biotin or glutamine were used for both absorbance and diffraction experiments. For the absorbance experiments, gel mixtures were prepared in a 0.1×SSC buffer. For the diffraction experiments, a 1×TBE buffer was used instead.

For the experiments run using glutamine, a 5 mL solution containing 0.2 mg/mL of streptavidin, $8.4 \times 10^{-4}$ M glutamine in 0.1×SSC buffer was prepared and used to form a 2.5% agarose gel following the conditions recommended in the Metaphor™ instruction sheet (Bio-Whittaker; Rockand, Me.). The gel mixture was gently heated in a microwave oven (MT-21105JQ; General Electric Corp.), mixed and stored as a stock solution. For experiments run using biotin, the same procedure described above was used except the final concentration of $8.4 \times 10^{-4}$ M biotin was achieved rather than $8.4 \times 10^{-4}$ M glutamine.

Example 2

Operation of Dual Compartment Absorbance Sensor to Monitor Binding of Biotin to Streptavidin An apparatus as shown in FIG. 2 was manufactured from Teflon® stock. A 220 nm xenon light source (Oriel Instruments, Stratford, Conn.) and a silica window (Quartz Scientific, Fairport, Ohio) placed between the light source and the second compartment generated a light beam with approximately 500 $\mu$Watt/0.95 cm$^2$ at 220 nm. An opening of 700 $\mu$m was placed in the first opaque elastomeric gasket 51 and provided transmission of $\frac{1}{240}^{th}$ of the incident radiation from the light source 44. A frame transfer CCD camera (Andor Technology, Belfast, N. Ireland) cooled to approximately −40° C. integrated the transmitted light between one to three seconds. The CCD pixels that were illuminated were recorded three times and averaged.

A platform, with mechanical stops, was placed before the CCD camera to allow reproducible positioning of the assembled diffusion sensor during operation. A reference measurement was made with each of the transmission measurements, and the difference was recorded. The reference measurement consisted of placing a 2 mm thick block of polydimethyl-siloxane (Dow-Corning) in the same spot on the platform reproducibly. To determine system sensitivity, an absorbance calibration curve was made with a dilution series prepared using glutamine in a 0.1×SSC buffer. The limit of detection was found to be 0.006 mg/mL of glutamine in 0.1×SSC buffer with a signal to noise ratio of two. Linear regression on the glutamine dilution series above produced a line-fit having y-intercept and slope corresponding to 45120 (CCD units/mg/ml) and −150600 (CCD units), with a correlation coefficient of 0.99306. With such a high correlation coefficient, it is reasonable to assume that the exponential dependence of the Beer-Lambert relation is sufficiently weak that it may safely replaced with a linear dependence. This relationship was used to convert the absorbance-versus-time data obtained from the leaching experiments into concentration-versus-time data for comparison with our model. Similarly, linear regression on the biotin dilution series above produced a line-fit having y-intercept and slope corresponding to 41770 (CCD units/mg/mL) and −125730 (CCD Units), with a correlation coefficient of 0.99616. These values were also used to perform the same conversion with the biotin absorbance-versus-time data.

To begin a new experiment, the first, upper Teflon™ compartment was placed on top of a flat microscope slide and a warm, 420-microliter aliquot of gel stock mixture was added to the central cavity. The compartment was then covered with a PDMS sheet to inhibit evaporation. While the top compartment/gel mixture was allowed to cool to room temperature, the bottom compartment was filled with 350-microliter of 0.1×SSC buffer. At room temperature, the top compartment/gel mixture was gently detached from the microscope slide using a fresh razor blade, and both compartments immediately assembled into the structure represented in FIG. 2. An initial transmission measurement was made, followed by successive measurements every ten minutes for the next three to four hours.

Figure 5:
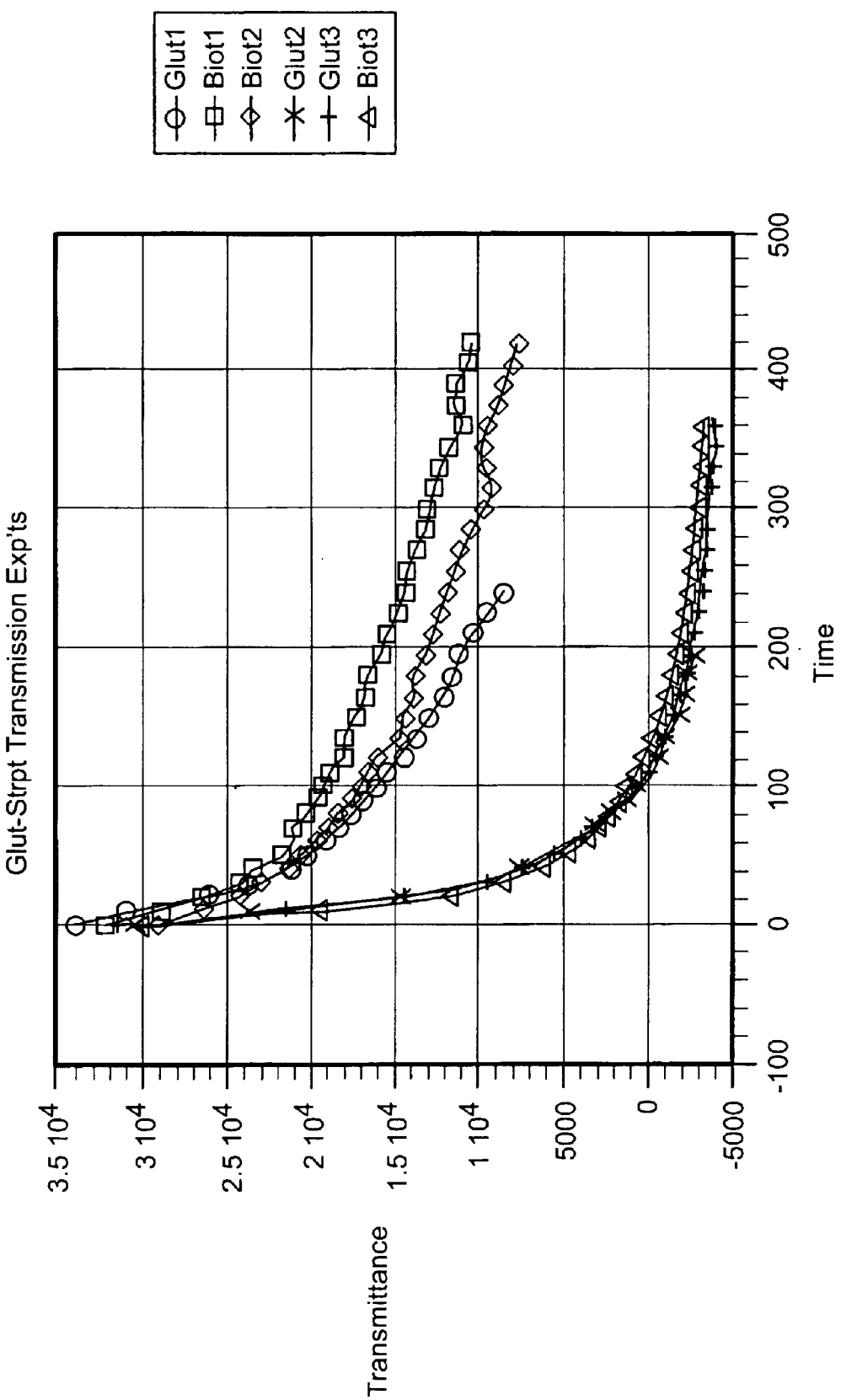
FIG. 5 is a graph showing a plot of transmittance versus time for the leaching of biotin and glutamine from an upstream compartment to a downstream compartment.

Referring now to FIG. 5, the six traces shown were obtained as follows. Each trace represents leaching of either biotin or glutamine from the top compartment/gel mixture into the bottom compartment (see FIG. 2) obtained by determining the absorbance of material in the bottom compartment as a function of time. After an initial absorbance determination was made (obtained immediately after assembly of both compartments), successive measurements were taken every ten minutes.

FIG. 5 shows the seemingly more rapid leach rate of the biotin. This feature is directly related to the stronger overall binding affinity of biotin to streptavidin ($K_d \sim 10^{-15}$M), which also manifests itself in the shape of the biotin traces. Strong binding is apparent in traces having sharp error function characteristics while poor binding exhibits a simple diffusional $t^{1/2}$ time dependence. Such dependence is apparent in FIG. 5 even before we transform the curves into concentration versus time traces. Another feature in FIG. 5 is the difference between the apparent reproducibility of the biotin traces when compared with the less reproducible glutamine traces. Since all the experiments were conducted in a similar manner, on different days, using the same glutamine-gel-streptavidin or biotin-gel-streptavidin stock solutions, it is believed that the variability in the glutamine traces maybe attributed more to specific glutamine-agarose interactions such as adsorption rather than experimental error or fluctuating physical properties such as temperature. However, the analysis is not significantly affected by the increased error dispersion of the glutamine traces, and we did not pursue the matter further.

Figure 6A:
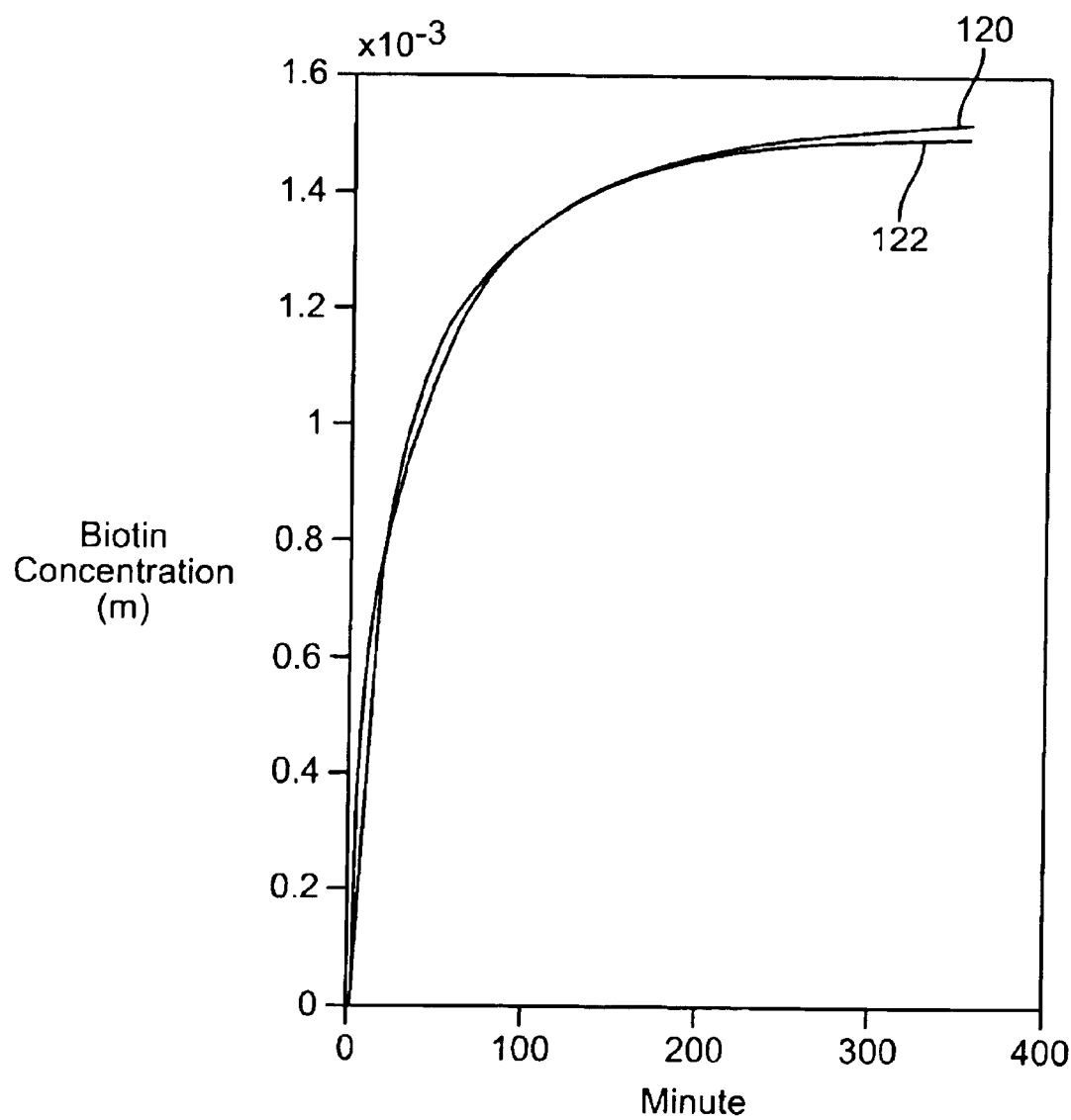
FIG. 6A is a graph showing a plot of biotin concentration in a downstream compartment versus time.
Figure 6B:
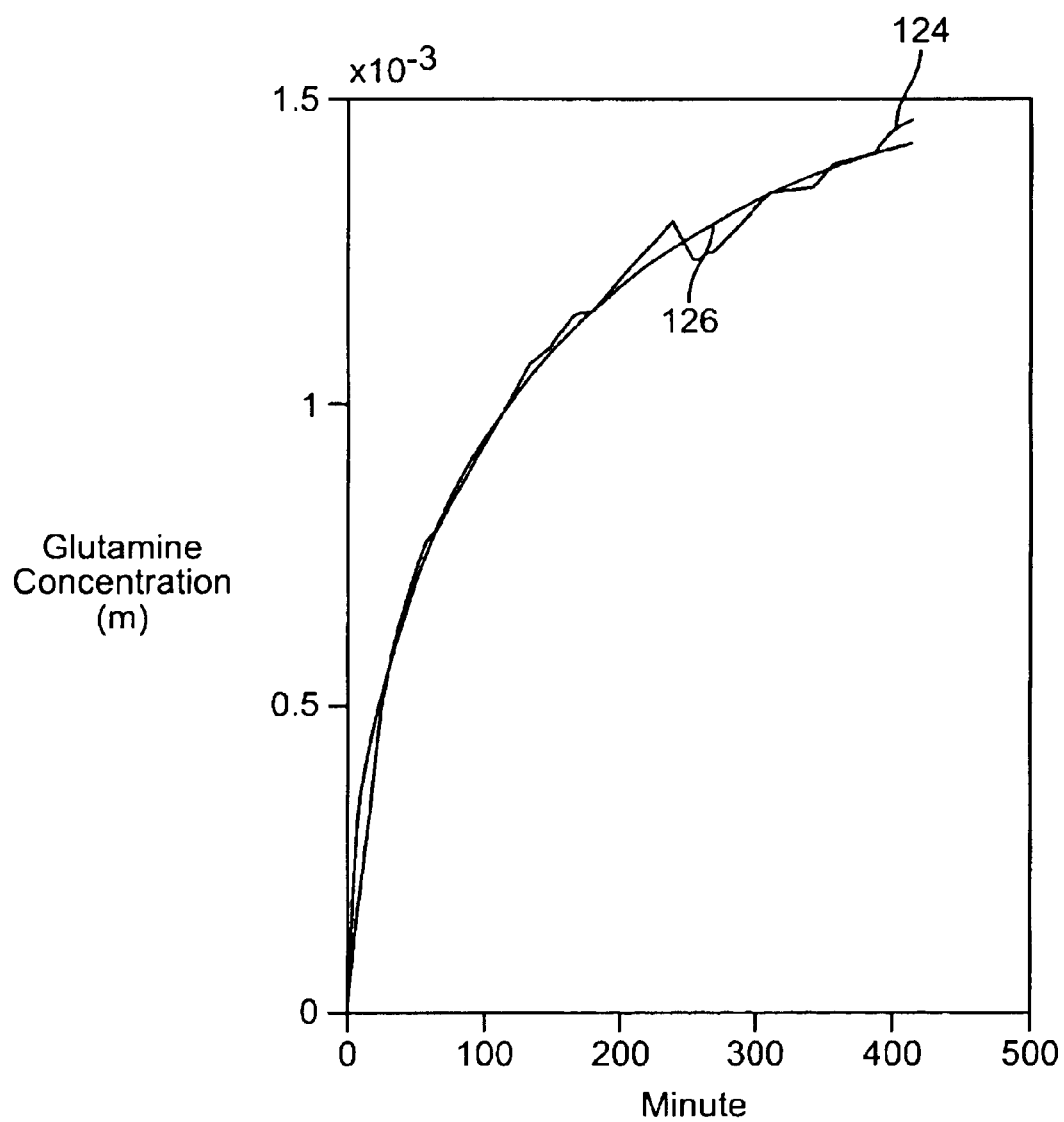
FIG. 6B is a graph showing a plot of glutamine concentration in a downstream compartment versus time.

To make connection with theory, the absorbance-time data is transformed to concentration-time data using the coefficients obtained from the linear curve-fit procedures described above. The results are shown in FIGS. 6A and 6B. In FIG. 6A, the curve 120 represents the average of all biotin traces and curve 122 represents the fit of equation 3 (above) to the curve 120. In FIG. 6B, curve 124 represents represents the average of all glutamine traces and curve 126 represents the fit. The Marquardt-Levenberg algorithm was used to model the data, and produced exceptionally good fits to equation 3 with low singular values of the residuals: $3.46 \times 10^{-8}$ and $3.35 \times 10^{-8}$ for biotin and glutamine runs respectively. The standard deviation associated with the curve fits were $3.35 \times 10^{-5}$ and $3.22 \times 10^{-5}$ for biotin and glutamine runs respectively; which is reassuring for the $10^{-3}$–$10^{-4}$ molar range spanned by the data. The high quality fits were produced using a simple two-parameter error fitting function: one parameter to multiply the error function in equation 3 and another parameter to represent the binding constant, k. This paucity of parameters that produce such high quality fits suggests the model and assumptions are reasonable descriptions of the dynamic processes at work. The values obtained for the fitting function, f=coefficient$_1$*Error_Function(coefficient$_2$*time$^{1/2}$), were: Biotin Traces~0.0015 M for coefficient$_1$, 0.1089 for coefficient$_2$, and Glutamine Traces~0.0016 M for coefficient$_1$, 0.0570 for coefficient$_2$. The relationship of coefficient$_2$ with the effective binding constant, k (see equation 3) yields k-values of 0.01186 min$^{-1}$ and 0.00325 min$^{-1}$ for biotin and glutamine traces respectively. While the higher binding constant belongs to the biotin curve-fits, it is only by a factor of 4. With a more sensitive system, it would be reasonable to expect a greater dynamic range between values for binding and non-specific binding.

Example 3

Figure 7A:
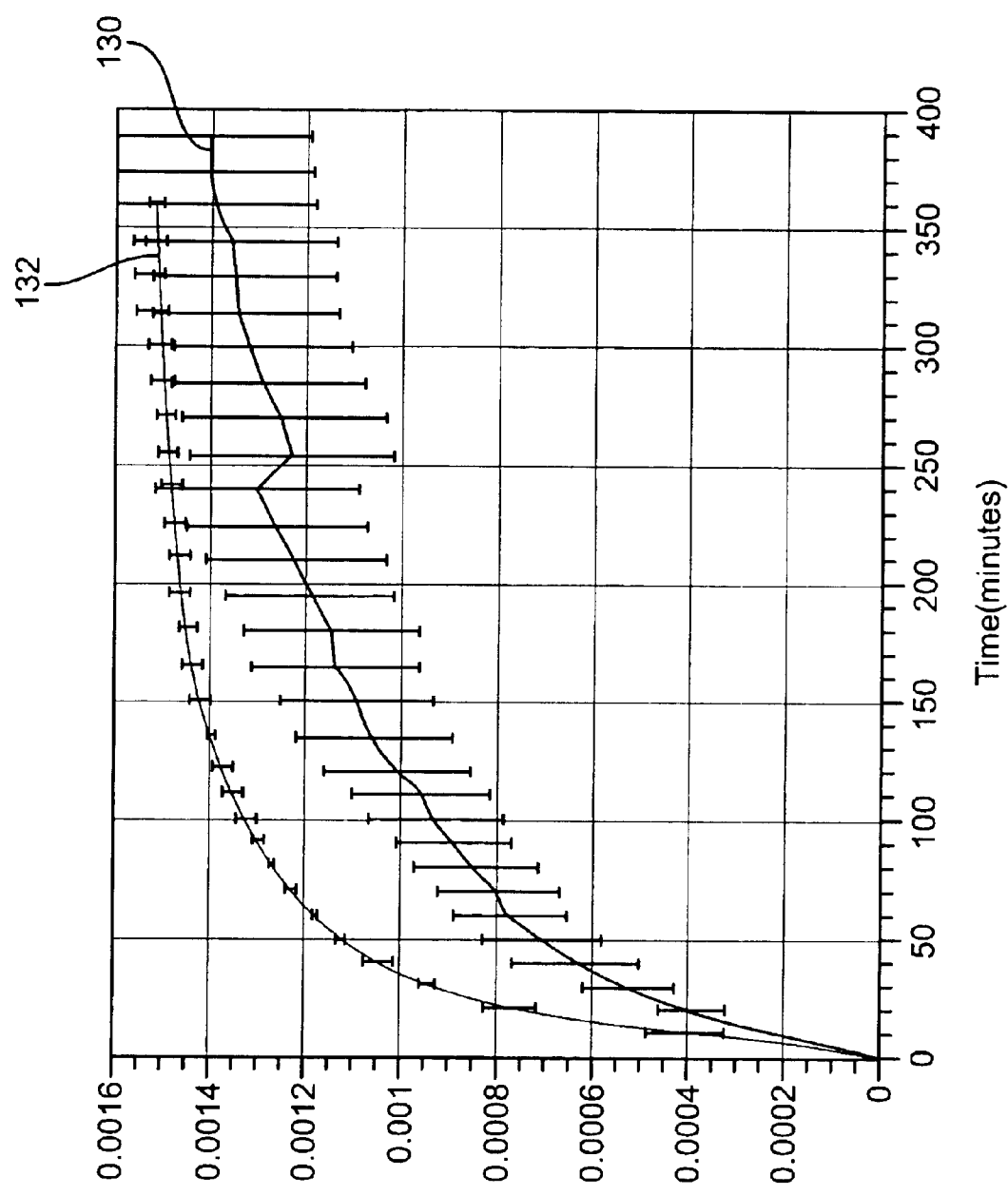
FIG. 7A is a graph showing a plot of diffusion of glutamine and biotin into a downstream compartment when streptavidin is in the upstream compartment.
Figure 7B:
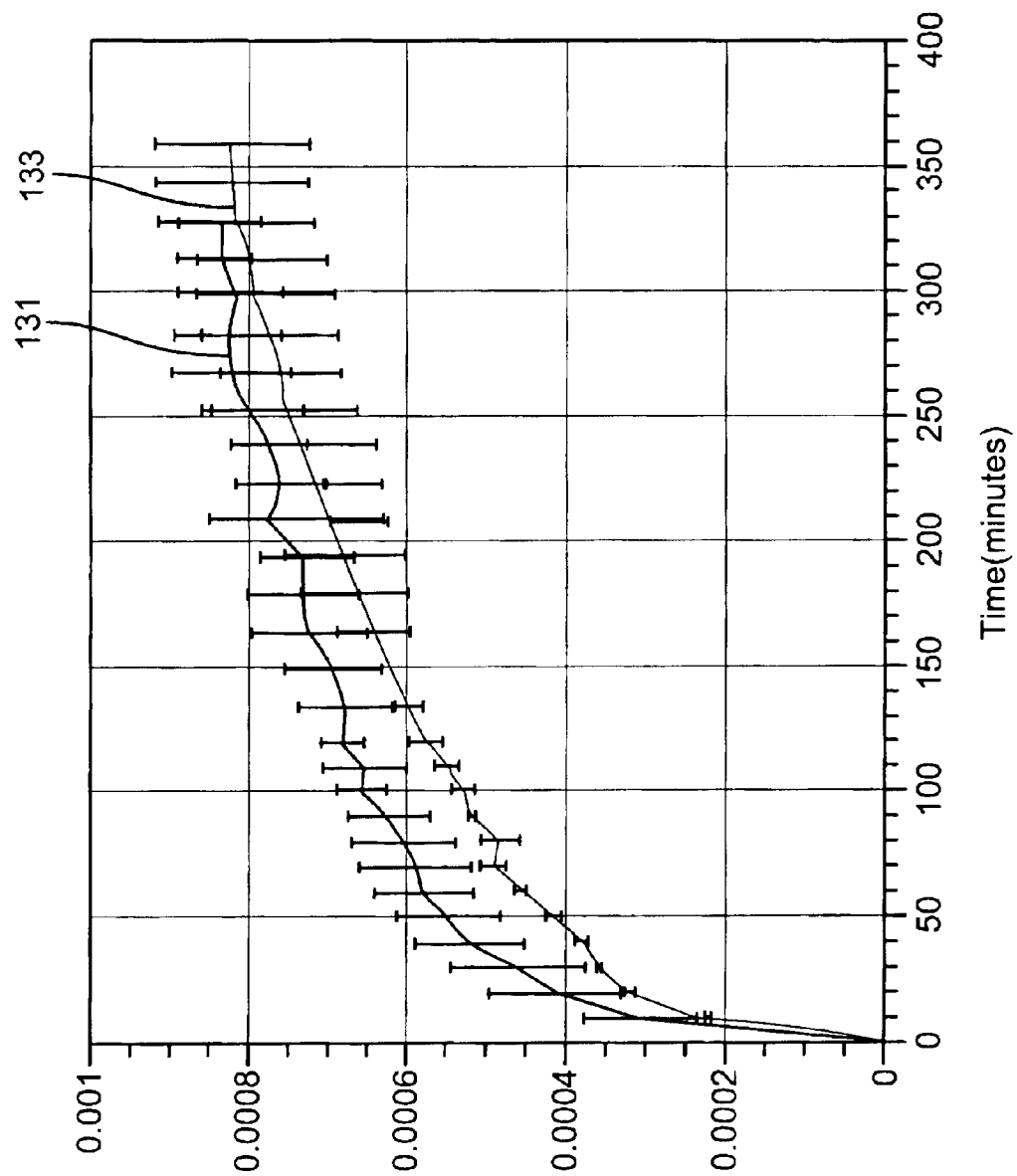
FIG. 7B is a graph showing a plot of diffusion of glutamine and biotin into a downstream compartment when streptavidin is in the upstream compartment when anti-biotin in the in upstream compartment.

Operation of Dual Compartment Absorbance Sensor to Monitor Binding of Antibodies to Streptavidin Another series of experiments was performed using antibodies to biotin (anti-biotin) instead of streptavidin to explore the lower limits of binding affinities still detectable using this process. These experiments were conducted identically in most every respect with the experiments described in Example 2 above, except for the different target protein used. Antibodies have $K_D$ values in the range, $\sim 10^{-6}$ M, much larger than streptavidin/biotin. As shown in FIGS. 7A and 7B, the binding affinities of glutamine 130, 132 and biotin 131, 133 were indistinguishable, implying that this particular experimental embodiment may not be able to distinguish small binding affinities due to limited detection sensitivity. It might be expected that lower concentrations all around, or at least with the biotin and glutamine, are required to inhibit the amount of non-specific binding present in the experiments.

Example 4

Sensing of Glutamine Diffusion Using a Three Slot Diffraction Sensor (3SDB)

Figure 8:
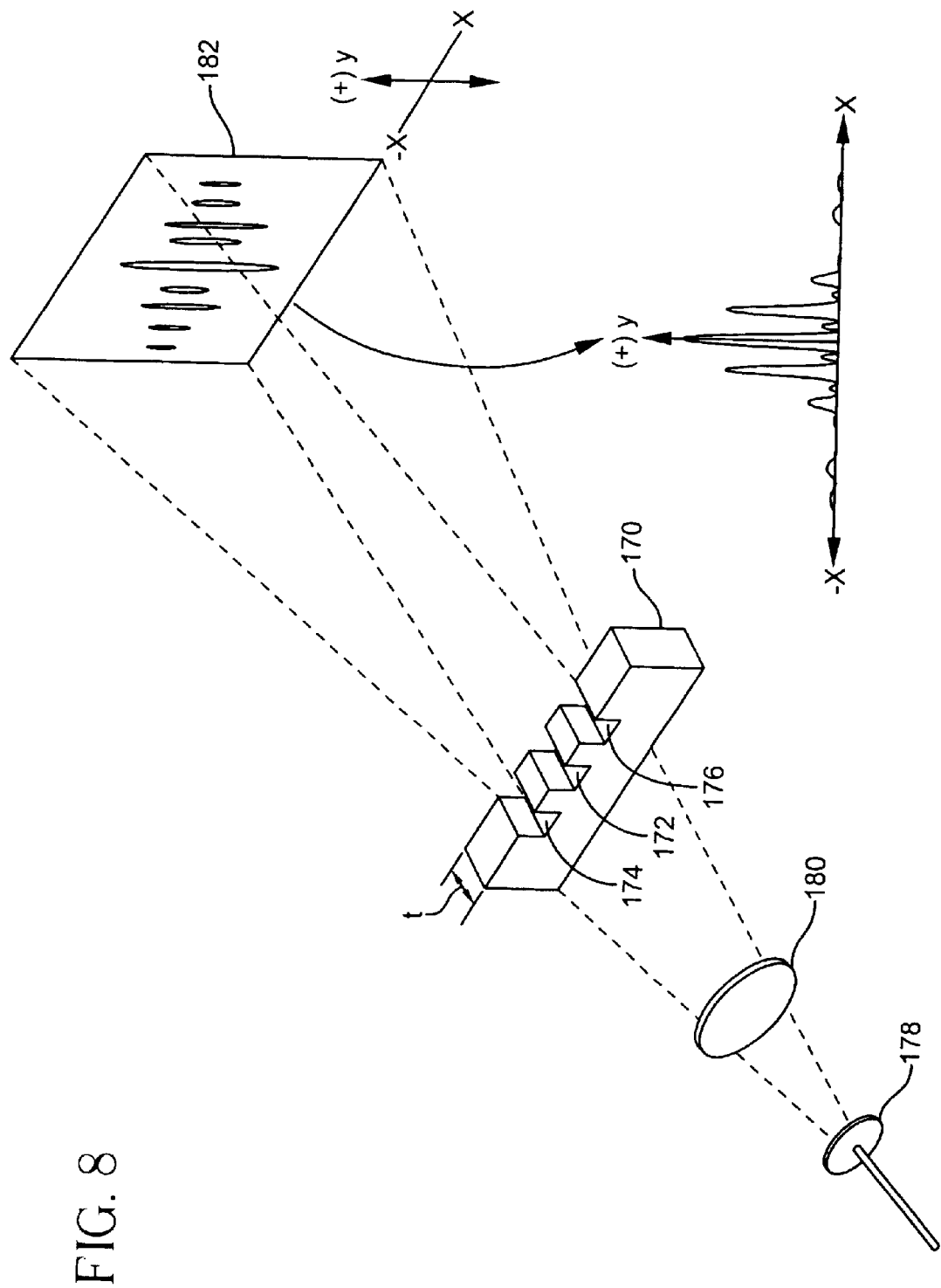
FIG. 8 is a schematic view of another embodiment of a diffraction sensor.

A schematic illustration of an example of a three-slot diffraction sensing prototype used to characterize the operation and sensitivity of the apparatus is shown in FIG. 8. Similar to the device shown in FIG. 3, a three slot diffractor 170 is provided including a central slot 172 and two outer slots 174 and 176. The contents of the outer slots 174 and 176 were kept constant while the contents of the central slot 172, and therefore the refractive index, were changed using a glutamine dilution series prepared in water for determination of device sensitivity. A light source 178 and a lens 180 generated a characteristic pattern 182 occurring in the far-field, which was measured by a CCD camera.

The characteristic pattern occurring in the far-field 82 was observed to change due to the amount of material placed in the central slot and changes precisely in the fashion described by equation 9. Two forms of the 3-slot diffraction sensor prototype were constructed differing only in the effective thickness (t) of the path length. The thickness' of these two prototypes (1 mm versus 13 mm) were used to determine the sensitivity and dynamic range.

Figure 9A:
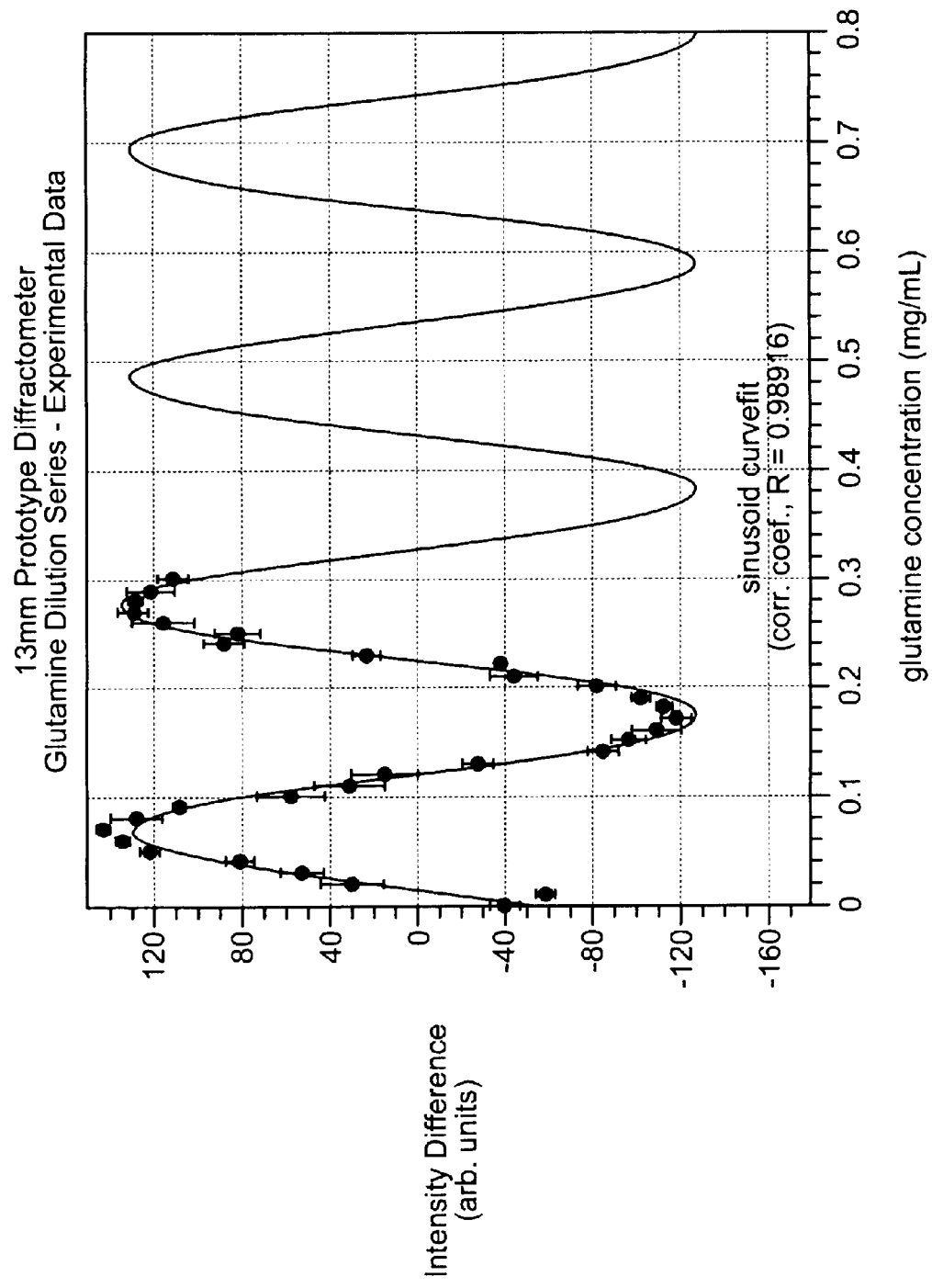
FIG. 9A is a graph showing the adjacent peak-to-peak intensity difference versus glutamine concentration for a 13 mm thick diffraction sensor.
Figure 9B:
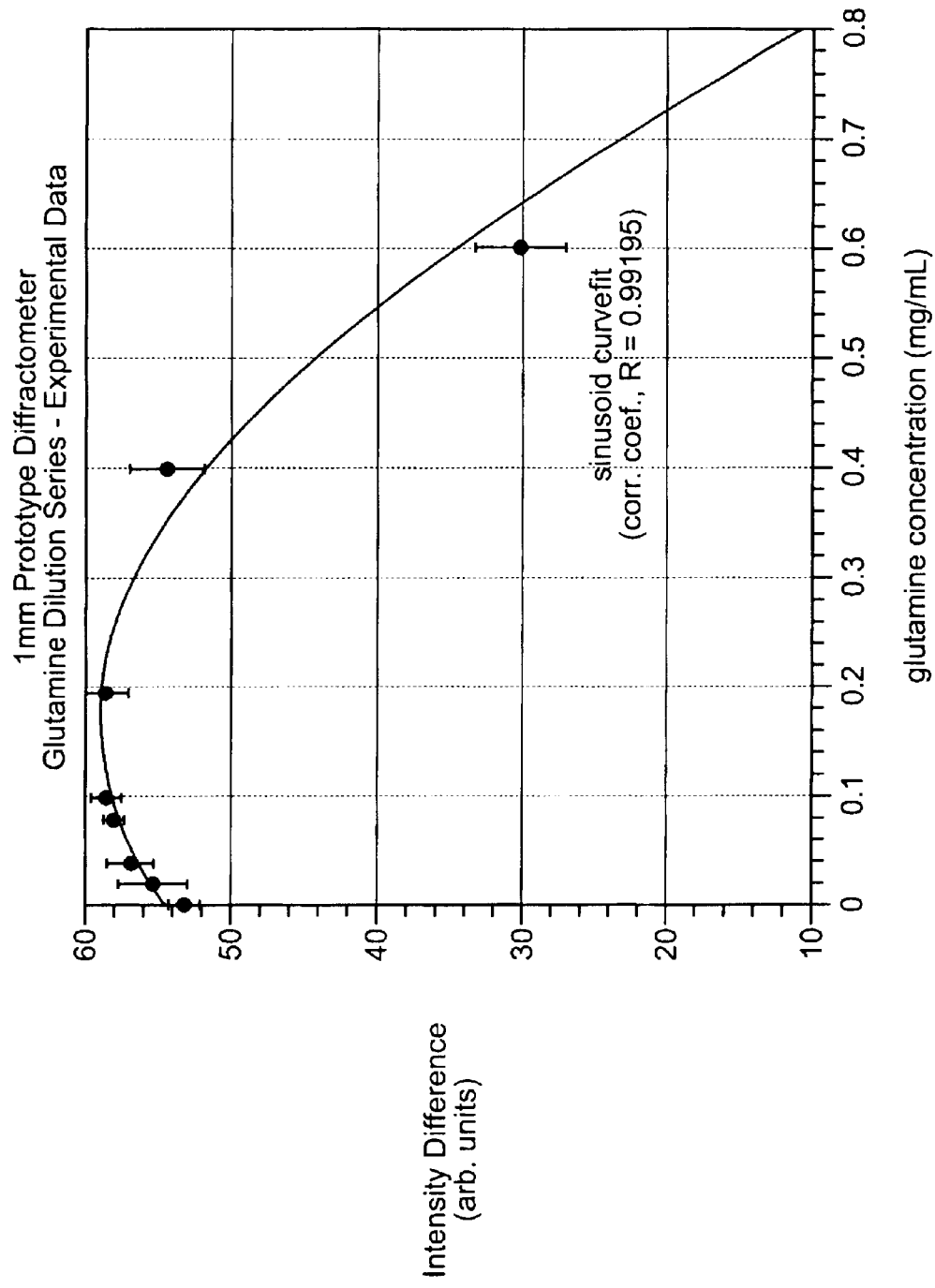
FIG. 9B is a graph showing the adjacent peak-to-peak intensity difference versus glutamine concentration for a 1 mm thick diffraction sensor.

The experimental results of these two 3SDB prototypes are shown in FIGS. 9A and 9B. An aqueous concentration series of glutamine was prepared, sequentially introduced into the central slot of both prototypes and the far-field pattern monitored at each concentration. The intensity difference between adjacent peaks was extracted out of the far-field pattern, statistics obtained and results plotted in FIGS. 9A and 9B. Glutamine was chosen as a drug analog because of its size (~140 Dalton) and molecular structure (amide-like), which are representative of potential drug attributes one might encounter in pharmaceutical high-throughput screening efforts. FIG. 9B demonstrates the wide dynamic range and reduced sensitivity of the 1 mm prototype while FIG. 9A shows the reduced dynamic range but superior sensitivity of the 13 mm prototype. Clearly, tradeoff of dynamic range and sensitivity are required in designing this sensor for a specific application. Similar dilution series were prepared using bovine serum albumin (BSA) validating the sinusoidal dependence of signal on weight-to-concentration variation. The results were indistinguishable with FIGS. 9A and 9B.

Separate glutamine dilution series were prepared exploring the limit of detection when the contents in the outer slots of the 1 mm and 13 mm prototypes were adjusted to operate in the linear, sensitive portion of the signal sinusoids. The limit of detection for the 13 mm prototype was 0.002 mg/mL with a S/N~2 and 0.01 mg/mL with a S/N~2 for the 1 mm prototype.

Example 5

Sensing of Leaching of Biotin and Glutamine Using a Diffraction Sensor

A schematic illustration of the three-slot diffraction sensing system used to characterize the drug-leaching experiments with biotin and glutamine is shown in FIG. 8. The characteristic pattern is captured in the far field by the CCD camera (same system used with absorbance experiments) at ten minute intervals and the resulting image is saved as a TIFF picture file. Those files are then converted into traces, imported into a spread-sheet program, Kaleidagraph, and the intensity differences are manually determined and recorded. Those differences are then plotted as a function of time and result in the sinusoidal waveform.

Figure 10:
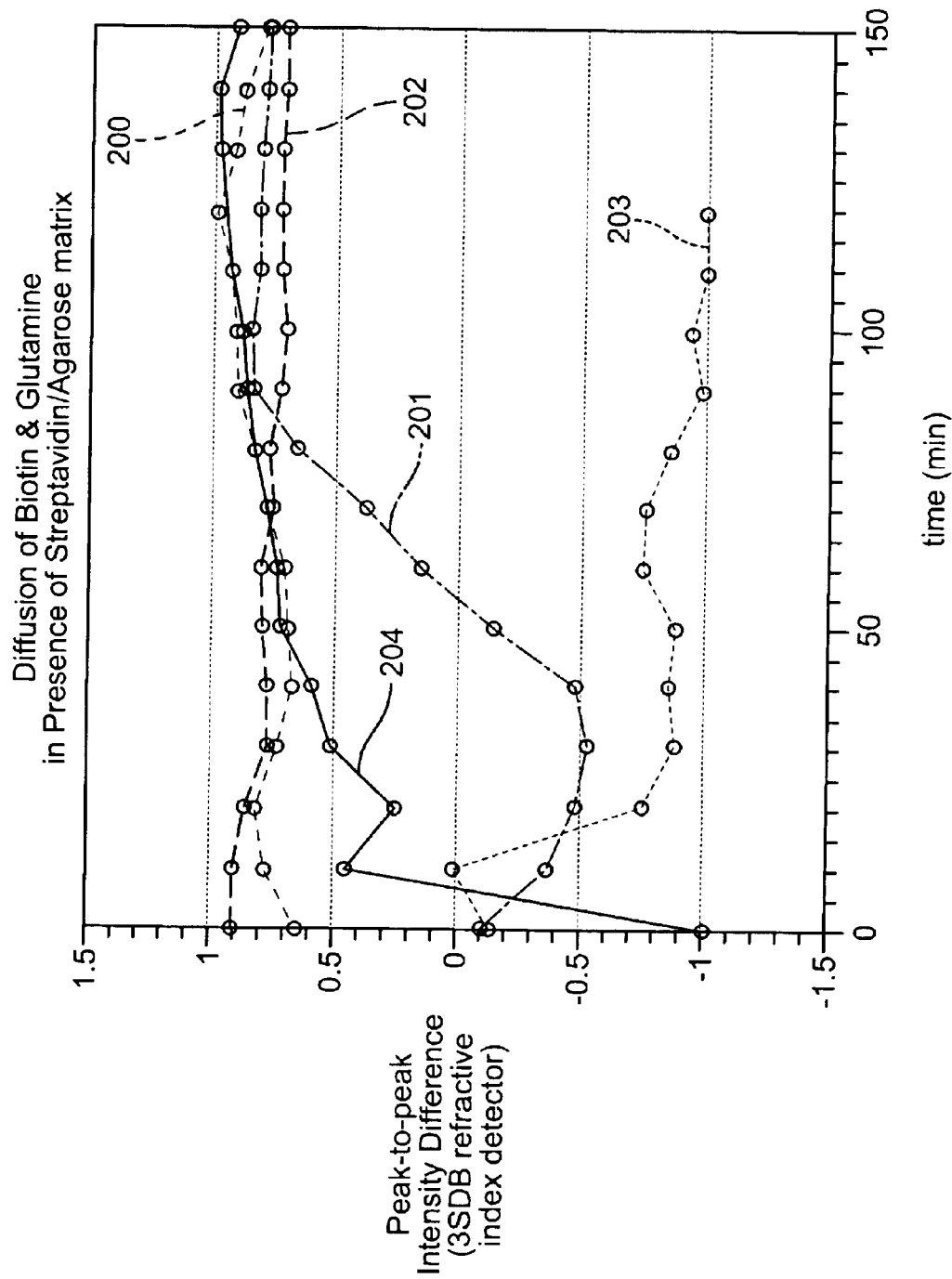
FIG. 10 is a graph showing peak-to-peak intensity difference versus time for biotin or glutamine leaching out of the central sensing area of a three slot diffraction sensor.

FIG. 10 shows the complex signal that results from biotin (three samples, 200, 202, 204) or glutamine (three samples, 201, 203, 205) leaching out of the central sensing volume of the three slot diffraction sensor under leaching conditions identical with previous experiments. While the signal-time series must be deconvolved into a concentration-time data series to obtain quantifiable results, one can still observe more activity in the biotin traces when compared with those of glutamine. This is consistent with the absorbance results where glutamine leaching was indeed much slower than biotin leaching, thus validating this alternative approach.

An advantage of the present invention is the ability to provide a truly homogeneous and label-free bio-assay for HTS. One can readily envision a set of two compartments, separated by a membrane permeable by small molecules on the order of 200 tO 1000 Dalton molecules. A dual compartment arrangement pre-filled with a suitable buffer, outfitted with a detachable lid, and having the capability to monitor the concentration in any one compartment with high sensitivity, would provide the basis for a high-throughput screening assay.

The current drive to miniaturize bioassay designs naturally lends itself to high-speed assays based on diffusional transport. A high-density array of miniature 2-compartment features in a 96-well or 384-well format is possible; it is also conceivable to arrange such an array to exploit the concept that diffusion may be used to determine pharmacokinetic parameters.

Thus the present invention provides a novel diffusional sensor having the ability to successfully distinguish strong versus weak binding events between ligand-receptor analogues. The present invention has demonstrated the ability analyze small drug—large protein interactions for drug molecular weights in the 200–1000 Dalton range and target proteins in the size range greater than 10 kDalton. The accumulation of ligand-analogue in the downstream compartments or departure of ligand-analogue from the central sensing volume of a diffraction sensor was found to be characteristic of the protein-binding affinity. The ability to provide relatively simple sensors having minimal dimensions (as low as 500 microns), without requiring sophisticated microfluidics make the prospects of producing high-density, high-throughput devices for drug-screening attractive.

It will be apparent to those skilled in the art that various modifications and variations can be made to the present invention without departing from the spirit or scope of the invention. For example, a variety of ligands and receptors may be analyzed in accordance with the present invention. For example, in addition to dual compartment arrangement described above, it is envisioned that a single compartment having an appropriate membrane in the single compartment could be utilized to monitor diffusion from a matrix containing ligands and receptors. Thus, it is intended that the present invention cover modifications and variations of this invention provided they come within the scope of the appended claims and their equivalents.

What is claimed is:

1. A molecular detection apparatus comprising:
    a first compartment containing at least a ligand or a receptor;
    a second compartment adjacent said first compartment;
    a boundary area disposed between said first and second compartments;
    a sensing area; and
    means for detecting the diffusion of a molecule proximate the sensing area;
    wherein said ligand is smaller than said receptor and wherein the boundary area includes a membrane operative to allow said ligands to pass therethrough and to prevent passage of said receptors.

2. The molecular detection apparatus of claim 1, further comprising a means for detecting a rate of diffusion of said molecule proximate the sensing area.

3. The molecular detection apparatus of claim 1, wherein said means for detecting the diffusion of the molecule proximate the sensing area further includes a means for detecting variation of molecular concentration as a result of diffusion and interaction proximate the sensing area.

4. The molecular detection apparatus of claim 1, wherein the first compartment contains a matrix material.

5. The molecular detection apparatus of claim 1, wherein said ligand is a drug molecule having a molecular weight less than 1000 Daltons.

6. The molecular detection apparatus of claim 5, wherein the receptor molecule has a molecular weight greater than 5 kiloDaltons.

7. The molecular detection apparatus of claim 6, wherein the receptor molecule includes a protein molecule.

8. The molecular detection apparatus of claim 7, wherein the second compartment contains a buffer solution.

9. The molecular detection apparatus of claim 8, wherein the means for measuring molecular concentration of the molecule further comprises an optical detector.

10. The molecular detection apparatus of claim 9, wherein the optical detector includes a light source and a light detector.

11. The molecular detection apparatus of claim 10, wherein the light source includes a UV light source, the light detector includes a charge-coupled device detector, and the optical detector is operative to measure the light absorbed by the second compartment.

12. The molecular detection apparatus of claim 2, wherein the means for measuring the variation of molecular concentration comprises a refractive index detector and a diffraction device including three laterally spaced openings in a substrate.

13. The molecular detection apparatus of claim 12, wherein the means for measuring the molecular concentration further comprises detecting the change in the far field diffraction pattern generated by the three laterally spaced openings.

14. The molecular detection apparatus of claim 13, wherein the three laterally spaced openings includes a central opening containing a ligand and a receptor in solution.

15. The molecular detection apparatus of claim 14, further including means for detecting the change in the concentration of the ligand or the receptor contained in the central opening.

16. The molecular detection apparatus of claim 15, wherein the means for detecting the change in concentration of ligand and the receptor comprises a charge-coupled device camera.

17. An apparatus for detecting interaction between a ligand and a receptor comprising:
    a first compartment containing a matrix, a ligand and a receptor; and
    a second compartment adjacent the first compartment, the second compartment containing a buffer solution; and
    a light source and a detector arranged to measure the diffusion of the ligand into the second compartment; wherein the ligand is a drug molecule having a molecular weight less than 1000 Daltons and the receptor has a molecular weight greater than 5 kiloDaltons.

18. The apparatus of claim 17, wherein the matrix includes a polymer.

19. The apparatus of claim 17, wherein the light source and the detector determines the amount of light absorbed in the second compartment.

20. An apparatus for measuring the interaction between a ligand and a receptor comprising:
    a light source;
    a detector; and
    a substrate including at least three laterally spaced optical openings adapted to generate a diffraction pattern;
    wherein the three-laterally spaced openings are positioned on the opposite surface of a substrate containing a Y-shaped element including a sensing area.

21. The apparatus of claim 20, wherein the three laterally spaced openings includes a central opening.

22. The apparatus of claim 20, wherein the sensing area of the Y-shaped element is optically aligned with the central opening.

23. A substrate for use in a biological sensing system comprising three laterally spaced openings adapted to generate a diffraction pattern; wherein a first surface contains the laterally spaced openings and a surface opposite the first surface includes a Y-shaped element including a sensing area optically aligned with the central opening.

24. The substrate of claim 23, wherein the three laterally spaced openings are adapted to generate a Fraunhofer diffraction pattern.

25. A method for analyzing biomolecular interactions comprising:
    providing a ligand and a receptor either within or proximate to a slotted diffraction surface;
    placing the ligand and the receptor in a Y-shaped element having a sensing area;
    detecting the diffusion of biomolecules.

26. The method of claim 25, wherein the diffraction surface comprises three laterally spaced slots.

27. The method of claim 25, further comprising monitoring the diffraction pattern generated by the diffraction surface.

28. The method of claim 25, further comprising providing a ligand and a receptor within or proximate a central slot.

29. The method of claim 25, further comprising filling the Y-shaped element with a solution.

30. The method of claim 29, further comprising electrokinetically pumping the ligand and the receptor across the sensing area.

31. A method of analyzing biomolecular interactions comprising:
    providing a ligand and a receptor either within or proximate to a slotted diffraction surface;
    placing the ligand and the receptor in a Y-shaped element having a sensing area; and
    monitoring the rate of diffusion of biomolecules from an upstream area towards a downstream area.

32. The method of claim 31, wherein the upstream area includes and upstream compartment containing a mixture of a ligand and a receptor separated from the downstream compartment by a membrane.

33. The method of claim 31, wherein the biomolecules are contained in a porous matrix.

34. The method of claim 31, wherein the downstream area includes means for measuring the absorbance of light in the downstream compartment.

* * * * *